(12) United States Patent
Publicover et al.

(10) Patent No.: US 8,929,589 B2
(45) Date of Patent: Jan. 6, 2015

(54) SYSTEMS AND METHODS FOR HIGH-RESOLUTION GAZE TRACKING

(75) Inventors: Nelson G. Publicover, Reno, NV (US); William C. Torch, Reno, NV (US); Christopher N. Spitler, Fernley, NV (US)

(73) Assignee: Eyefluence, Inc., Reno, NV (US)

( * ) Notice: Subject to any disclaimer, the term of this patent is extended or adjusted under 35 U.S.C. 154(b) by 550 days.

(21) Appl. No.: 13/290,948

(22) Filed: Nov. 7, 2011

(65) Prior Publication Data

US 2013/0114850 A1     May 9, 2013

(51) Int. Cl.
*G06K 9/00*     (2006.01)
*A61B 3/113*     (2006.01)

(52) U.S. Cl.
CPC ............ *A61B 3/113* (2013.01); *G06K 9/00604* (2013.01)
USPC ....................................................... 382/103

(58) Field of Classification Search
CPC .......... G06K 9/00335; G06K 9/00597; G06K 9/00604; G06K 9/2027; G06K 9/209; G06K 2009/2045; G06K 2209/401; G06T 7/0022; G06T 7/004; G06T 2207/30041; A61B 3/0008; A61B 3/113; A61B 3/145
USPC ......... 382/100, 103, 117; 348/78; 345/8, 156, 345/157, 158; 351/209, 210
See application file for complete search history.

(56) References Cited

U.S. PATENT DOCUMENTS

| | | | |
|---|---|---|---|
| 4,439,157 A | 3/1984 | Breglia et al. | 434/40 |
| 4,568,159 A | 2/1986 | Baldwin | 351/210 |
| 4,595,990 A | 6/1986 | Garwin et al. | 364/518 |
| 4,852,988 A | 8/1989 | Velez | 351/210 |
| 4,950,069 A | 8/1990 | Hutchinson | 351/210 |
| 5,231,674 A | 7/1993 | Cleveland et al. | 382/6 |
| 5,331,149 A | 7/1994 | Spitzer et al. | 250/221 |

(Continued)

FOREIGN PATENT DOCUMENTS

| | | | | |
|---|---|---|---|---|
| CN | 101807110 A | 8/2010 | | G06F 3/01 |
| CN | 101901485 A | 12/2010 | | G06T 7/00 |

(Continued)

OTHER PUBLICATIONS

PCT International Search Report and Written Opinion for PCT/US2012/063973, Applicant: EYE-COM Corporation, Forms PCT/ISA/220, PCT/ISA/210 and PCT/ISA/237, dated Mar. 20, 2013, 11 pages.

*Primary Examiner* — Andrew W Johns
(74) *Attorney, Agent, or Firm* — William A. English; Vista IP Law Group LLP

(57) ABSTRACT

A system is mounted within eyewear or headwear to unobtrusively produce and track reference locations on the surface of one or both eyes of an observer. The system utilizes multiple illumination sources and/or multiple cameras to generate and observe glints from multiple directions. The use of multiple illumination sources and cameras can compensate for the complex, three-dimensional geometry of the head and anatomical variations of the head and eye region that occurs among individuals. The system continuously tracks the initial placement and any slippage of eyewear or headwear. In addition, the use of multiple illumination sources and cameras can maintain high-precision, dynamic eye tracking as an eye moves through its full physiological range. Furthermore, illumination sources placed in the normal line-of-sight of the device wearer increase the accuracy of gaze tracking by producing reference vectors that are close to the visual axis of the device wearer.

18 Claims, 7 Drawing Sheets

(56) References Cited

U.S. PATENT DOCUMENTS

| | | | |
|---|---|---|---|
| 5,345,281 A | 9/1994 | Taboada et al. | 351/210 |
| 5,367,315 A | 11/1994 | Pan | 345/156 |
| 5,430,505 A | 7/1995 | Katz | 351/208 |
| 5,471,542 A | 11/1995 | Ragland | 382/128 |
| 5,481,622 A | 1/1996 | Gerhardt et al. | 382/103 |
| 5,517,021 A | 5/1996 | Kaufman et al. | 250/221 |
| 5,583,590 A | 12/1996 | Clupper | 351/200 |
| 5,583,795 A | 12/1996 | Smyth | 364/516.444 |
| 5,585,871 A | 12/1996 | Linden | 351/158 |
| 5,689,241 A | 11/1997 | Clarke, Sr. et al. | 340/575 |
| 5,708,862 A | 1/1998 | Tsunekawa et al. | 396/51 |
| 5,861,936 A | 1/1999 | Sorenson | 351/200 |
| 6,088,470 A | 7/2000 | Camus et al. | 382/117 |
| 6,091,546 A | 7/2000 | Spitzer | 359/618 |
| 6,152,563 A | 11/2000 | Hutchinson et al. | 351/209 |
| 6,204,828 B1 | 3/2001 | Amir et al. | 345/7 |
| 6,252,977 B1 | 6/2001 | Salganicoff et al. | 382/117 |
| 6,282,553 B1 | 8/2001 | Flickner et al. | 708/141 |
| 6,346,887 B1 | 2/2002 | Van Orden et al. | 340/575 |
| 6,373,961 B1 | 4/2002 | Richardson et al. | 382/103 |
| 6,433,759 B1 | 8/2002 | Richardson et al. | 345/7 |
| 6,433,760 B1 | 8/2002 | Vaissie et al. | 345/8 |
| 6,511,424 B1 | 1/2003 | Moore-Ede et al. | 600/300 |
| 6,577,329 B1 | 6/2003 | Flickner et al. | 345/774 |
| 6,614,408 B1 | 9/2003 | Mann | 345/8 |
| 6,637,883 B1 | 10/2003 | Tengshe et al. | 351/210 |
| 6,659,611 B2 | 12/2003 | Amir et al. | 351/210 |
| 6,758,563 B2 | 7/2004 | Levola | 351/209 |
| 6,847,336 B1 | 1/2005 | Lemelson et al. | 345/8 |
| 6,864,912 B1 | 3/2005 | Mahaffey et al. | 348/61 |
| 6,873,314 B1 | 3/2005 | Campbell | 345/156 |
| 6,886,137 B2 | 4/2005 | Peck et al. | 715/785 |
| 6,919,907 B2 | 7/2005 | Berstis | 345/619 |
| 6,927,694 B1 | 8/2005 | Smith et al. | 340/576 |
| 6,959,102 B2 | 10/2005 | Peck | 382/103 |
| 6,997,556 B2 | 2/2006 | Pfleger | 351/246 |
| 7,043,056 B2 | 5/2006 | Edwards et al. | 382/103 |
| 7,071,831 B2 | 7/2006 | Johns | 340/576 |
| 7,120,880 B1 | 10/2006 | Dryer et al. | 715/863 |
| 7,130,447 B2 | 10/2006 | Aughey et al. | 382/103 |
| 7,145,550 B2 | 12/2006 | Gehlot et al. | 345/157 |
| 7,197,165 B2 | 3/2007 | Ryan | 382/103 |
| 7,206,022 B2 | 4/2007 | Miller et al. | 348/333.03 |
| 7,206,435 B2 | 4/2007 | Fujimura et al. | 382/117 |
| 7,306,337 B2 | 12/2007 | Ji et al. | 351/209 |
| 7,331,671 B2 | 2/2008 | Hammomd | 351/210 |
| 7,365,738 B2 | 4/2008 | Molander et al. | 345/157 |
| 7,391,887 B2 | 6/2008 | Durnell | 382/117 |
| 7,391,888 B2 | 6/2008 | Hu et al. | 382/118 |
| 7,401,920 B1 | 7/2008 | Krantz et al. | 351/210 |
| 7,414,791 B2 | 8/2008 | Urakawa et al. | 359/630 |
| 7,480,396 B2 | 1/2009 | Teiwes et al. | 382/117 |
| 7,522,344 B1 | 4/2009 | Curatu et al. | 359/634 |
| 7,542,210 B2 | 6/2009 | Chirieleison, Sr. | 359/630 |
| 7,556,377 B2 | 7/2009 | Beymer | 351/210 |
| 7,561,143 B1 | 7/2009 | Milekie | 345/156 |
| 7,572,008 B2 | 8/2009 | Elvesjo et al. | 351/206 |
| 7,580,545 B2 | 8/2009 | Venkatesh | 382/103 |
| 7,600,873 B2 | 10/2009 | Grundig | 351/210 |
| 7,616,125 B2 | 11/2009 | Johns | 340/576 |
| 7,646,422 B2 | 1/2010 | Kisacanin et al. | 348/370 |
| 7,653,213 B2 | 1/2010 | Longhurst et al. | 382/103 |
| 7,657,062 B2 | 2/2010 | Pilu | 382/103 |
| 7,676,063 B2 | 3/2010 | Cohen et al. | 382/103 |
| 7,736,000 B2 | 6/2010 | Enriquez et al. | 351/210 |
| 7,747,068 B1 | 6/2010 | Smyth et al. | 382/154 |
| 7,783,077 B2 | 8/2010 | Miklos et al. | 385/103 |
| 7,809,160 B2 | 10/2010 | Vertegaal et al. | 382/103 |
| 7,815,311 B2 | 10/2010 | Johns et al. | 351/209 |
| 7,819,525 B2 | 10/2010 | Connell, II | 351/204 |
| 7,832,866 B2 | 11/2010 | Chao | 351/209 |
| 7,844,086 B2 | 11/2010 | Hu et al. | 382/118 |
| 7,963,652 B2 | 6/2011 | Vertegaal et al. | 351/205 |
| 7,986,816 B1 | 7/2011 | Hoanca et al. | 382/115 |
| 8,025,405 B2 | 9/2011 | Rehnstrom | 35/210 |
| 8,048,065 B2 | 11/2011 | Grecu et al. | 606/10 |
| 8,064,647 B2 | 11/2011 | Bazakos et al. | 382/117 |
| 8,135,173 B2 | 3/2012 | Chao | 382/103 |
| 8,165,347 B2 | 4/2012 | Heinzmann et al. | 382/103 |
| 8,185,845 B2 | 5/2012 | Bjorklund et al. | 715/863 |
| 8,220,926 B2 | 7/2012 | Blixt et al. | 351/210 |
| 8,225,229 B2 | 7/2012 | Thorn et al. | 715/802 |
| 2002/0118339 A1 | 8/2002 | Lowe | 351/209 |
| 2003/0043268 A1 | 3/2003 | Mann | 348/143 |
| 2004/0061680 A1 | 4/2004 | Taboada | 345/157 |
| 2004/0183749 A1 * | 9/2004 | Vertegaal | 345/7 |
| 2004/0239878 A1 | 12/2004 | Bradley | 351/237 |
| 2005/0047629 A1 | 3/2005 | Farrell et al. | 382/117 |
| 2006/0110008 A1 | 5/2006 | Vertegaal et al. | 382/103 |
| 2006/0147094 A1 | 7/2006 | Yoo | 382/117 |
| 2007/0105071 A1 | 5/2007 | Weatherhead | 434/81 |
| 2007/0299362 A1 | 12/2007 | Epley et al. | 600/559 |
| 2008/0137909 A1 | 6/2008 | Lee et al. | 382/103 |
| 2008/0166052 A1 | 7/2008 | Hatano | 382/190 |
| 2009/0196460 A1 | 8/2009 | Jakobs et al. | 382/103 |
| 2009/0315827 A1 | 12/2009 | Elvesjo et al. | 345/157 |
| 2010/0128118 A1 | 5/2010 | Swindells et al. | 348/78 |
| 2010/0245093 A1 | 9/2010 | Kobetski et al. | 340/576 |
| 2010/0295774 A1 | 11/2010 | Hennessey | 345/156 |
| 2010/0322479 A1 | 12/2010 | Cleveland | 382/103 |
| 2010/0328444 A1 | 12/2010 | Blixt et al. | 348/78 |
| 2011/0013007 A1 | 1/2011 | Holmberg et al. | 348/78 |
| 2011/0019874 A1 | 1/2011 | Jarvenpaa et al. | 382/103 |
| 2011/0037850 A1 | 2/2011 | Tsou | 348/143 |
| 2011/0043644 A1 | 2/2011 | Munger et al. | 348/207.1 |
| 2011/0077546 A1 | 3/2011 | Fabian | 600/544 |
| 2011/0077548 A1 | 3/2011 | Torch | 600/558 |
| 2011/0085139 A1 | 4/2011 | Blixt et al. | 351/209 |
| 2011/0121976 A1 | 5/2011 | Johns et al. | 340/576 |
| 2011/0170061 A1 | 7/2011 | Gordon | 351/206 |
| 2011/0175932 A1 | 7/2011 | Yu et al. | 345/661 |
| 2011/0182472 A1 | 7/2011 | Hansen | 382/103 |
| 2011/0199202 A1 | 8/2011 | De Mers et al. | 340/439 |
| 2011/0228975 A1 | 9/2011 | Hennessey et al. | 382/103 |
| 2011/0262887 A1 | 10/2011 | Cleveland | 434/247 |
| 2011/0279666 A1 | 11/2011 | Strombom et al. | 348/78 |
| 2011/0310006 A1 | 12/2011 | Edwards et al. | 345/156 |
| 2012/0007772 A1 | 1/2012 | Parssinen et al. | 342/176 |
| 2012/0038629 A1 | 2/2012 | Brown et al. | 345/419 |
| 2012/0052597 A1 | 3/2012 | Landgraf et al. | 436/518 |
| 2012/0057129 A1 | 3/2012 | Durnell et al. | 351/210 |
| 2012/0068913 A1 | 3/2012 | Bar-Zeev et al. | 345/8 |
| 2012/0105486 A1 | 5/2012 | Lankford et al. | 345/661 |
| 2012/0133891 A1 * | 5/2012 | Jiang | 351/210 |
| 2012/0147328 A1 | 6/2012 | Yahav | 351/210 |
| 2012/0154277 A1 | 6/2012 | Bar-Zeev et al. | 345/158 |

FOREIGN PATENT DOCUMENTS

| | | | | |
|---|---|---|---|---|
| EP | 0125808 | A2 | 11/1984 | A61B 3/10 |
| EP | 1 403 680 | A1 * | 3/2004 | G02B 27/01 |
| GB | 2284582 | A | 6/1995 | G08B 21/00 |
| GB | 2390425 | A | 9/2004 | G08B 21/06 |
| JP | 2002143094 | A | 5/2002 | A61B 3/113 |
| JP | 2004310470 | A | 11/2004 | G06F 3/033 |
| KR | 100949743 | B1 * | 3/2010 | G06F 3/00 |
| NL | 1021496 | C | 3/2004 | A61B 5/18 |
| TW | 200947262 | | 11/2009 | G06F 3/01 |
| TW | 201001236 | | 1/2010 | G06F 3/033 |
| WO | 9849028 | | 11/1998 | B60Q 1/00 |
| WO | 9905988 | A2 | 2/1999 | |
| WO | 02067067 | A2 | 8/2002 | G05B 1/409 |
| WO | 2007092512 | A2 | 8/2007 | |
| WO | 2011024134 | A1 | 3/2011 | A61B 3/113 |
| WO | 2012021967 | A1 | 2/2012 | H04H 13/00 |
| WO | 2012083415 | A1 | 6/2012 | G06F 3/048 |

* cited by examiner

SYSTEMS AND METHODS FOR HIGH-RESOLUTION GAZE TRACKING

STATEMENT REGARDING FEDERALLY SPONSORED RESEARCH AND DEVELOPMENT

The U.S. Government may have a paid-up license in this invention and the right in limited circumstances to require the patent owner to license others on reasonable terms as provided for by the terms of Department of Defense (US Army) Contract No. W81XWH-05-C-0045, U.S. Department of Defense Congressional Research Initiatives No. W81XWH-06-2-0037, W81XWH-09-2-0141, and W81XWH-11-2-0156; and U.S. Department of Transportation Congressional Research Initiative Agreement Award No. DTNH 22-05-H-01424.

FIELD OF THE INVENTION

The present invention relates to apparatus, systems, and methods for producing accurate gaze tracking using an unobtrusive eyewear or headwear device for eye monitoring and/or control applications.

BACKGROUND OF THE INVENTION

The systems and methods herein utilize machine vision techniques to track the locations and/or objects being viewed by an observer. Traditionally, gaze tracking algorithms have been considered as requiring two continuous data streams in order to produce tracking results: 1) head tracking methods to locate the position and orientation of the head within our three-dimensional world, and 2) eye tracking methods to detect glints produce by illumination sources along with the edges of pupils or other identifiable reference points on the surface of the eye to compute pivot angles and viewing directions of the eye relative to those glints. For accurate gaze tracking using an unobtrusive eyewear or headwear device, continually monitoring the position (relative to the surface of an eye) of the device itself including all cameras and illumination sources affixed to the device is an additional input to account for individual variations in head anatomy as well as small movements of the eyewear or headwear during use.

Applications that involve machine vision are becoming increasingly common-place. In part, this has arisen as a result of technological advances in the electronics and software development industries, and decreases in the cost of cameras, information processing units, and other electronic components. Gaze tracking, in particular, is increasingly being used in a number of diagnostic, human performance, and control applications. A small number of examples include monitoring the degree of fatigue of an individual, assessing driver or pilot awareness, assessing the effects of drugs or alcohol, diagnosing post-traumatic stress disorder, tracking human performance with age, determining the effectiveness of training or exercise on performance, assessing the effectiveness of television advertising or web-page designs by measuring ocular dwell times, magnifying or changing the brightness of specific objects or images (including words and sentences) under observation, controlling various aspects of games, acquiring foundational clinical data to assess neurological or cognitive disorders, diagnosing and monitoring degenerative eye conditions, and allowing individuals with limited or no mobility below the neck to communicate by controlling a computer cursor using one or more eyes and eyelids. Sectors and industries that utilize gaze tracking include military, medicine, security, human performance, gaming, sports medicine, rehabilitation engineering, police, research laboratories, and toys.

In almost all cases, an increase in the accuracy of gaze tracking leads to an increase in both the performance and ease-of-use of most applications. For example, with increased accuracy, ocular dwell times to quantify locations and fixation times on smaller objects or components of objects can be more accurately measured. Gaze tracking can be more effectively employed with portable devices that utilize smaller screens including mobile phones and hand-held displays. When gaze tracking is used to control a computer cursor involving the selection from a number of virtual objects or icons within a screen, an increased number of selectable objects can be displayed simultaneously because of the ability to choose smaller virtual objects or icons. An increased number of objects within each level of a selection process may increase the efficiency (i.e., reduced number of selection levels and/or reduced time) that a virtual object and associated action can be chosen.

With the advent of modern-day microelectronics and micro-optics, it is possible to unobtrusively mount the components for gaze tracking on eyewear (e.g., an eyeglass frame) or headwear (e.g., helmets, masks, goggles, virtual reality displays) including devices, such as those disclosed in U.S. Pat. No. 6,163,281, 6,542,081, or 7,488,294, 7,515,054, the entire disclosures of which are expressly incorporated by reference herein. Methods related to head tracking where one or more device-mounted scene cameras are used to tracking reference locations within our environment are disclosed in application Ser. No. 13/113,003, filed May 20, 2011, the entire disclosure of which is expressly incorporated by reference herein. Methods related to controlling the illumination of a scene based on camera images are disclosed in application Ser. No. 12/715,177, filed Mar. 1, 2010, the entire disclosure of which is expressly incorporated by reference herein. Methods related to measuring responses and reaction times of a device wearer are disclosed in application Ser. No. 13/113,006, filed May 20, 2011, the entire disclosure of which is expressly incorporated by reference herein; where improvements in spatial accuracy, as described in the present application, may contribute to improvements in the temporal accuracy of reaction time measurements.

Structures and reflections on the surface of the eye as well as the scene viewed by a device wearer may be imaged using high-precision micro-optics affixed to cameras within eyewear or headwear systems. The use of low-power, miniature cameras and electronics permits a full range of motion using a head-mounted system that is either tethered to other devices or non-tethered and (optionally) powered by a battery. Furthermore, recent advances in wireless telecommunications allow gaze tracking results to be transmitted in real-time to other computing, data storage, and/or control devices. As a result of these technological advances in a number of fields, an eyewear- or headwear-based gaze tracking system may be unobtrusive, light-weight, portable, and convenient to use with unrestricted mobility.

SUMMARY OF THE INVENTION

The present invention is directed to apparatus, systems, and methods for producing accurate gaze tracking using an unobtrusive eyewear or headwear device for eye monitoring and/or control applications, e.g., using multiple eye-tracking cameras.

The use of multiple eye tracking cameras mounted on eyewear or headwear, a component of the systems and methods of the present application, may have a number of advantages over a single camera affixed to headwear or multiple cameras located some distance away from the head. First, cameras directed at the eye from different angles may be used in a "range-finder" mode to track the locations of glints produced by illumination sources. The positions of a glint viewed from multiple angles may be used to determine camera position relative to the surface of an eye. This may be particularly useful to account for initial positions and movements of eyewear or headwear during use. Second, an individual camera directed at an eye produces two-dimensional images, whereas movements of the eyeball and other structures (e.g., eyelids, facial muscles) take place in all three (3) spatial dimensions. Image measurements from multiple cameras that view an eye from different directions may be used within anatomical model-based approaches to virtually reconstruct movements of the eye and other reference locations (e.g., glints, eye lids) in all dimensions. Third, extreme movements of the eye (i.e., up or down, left or right) may result in distortions in the ability to accurately track a pupil or other reference locations, or even the complete loss of the ability observe a pupil by a single, near-field camera due to the curvature of the eyeball and/or interference by other structures. The use of multiple cameras may permit more accurate tracking of pupils and other reference locations over a complete physiological range of eye positions.

The use of multiple illumination sources mounted on eyewear or headwear and directed at the eye may have a number of further advantages over an individual illumination source affixed to headwear or one or more illumination sources located some distance away from the head. For example, the use of multiple illumination sources may ensure that all regions around the three-dimensional structures of the eye are adequately illuminated without the production of shadows or other artifacts that confound machine image-processing algorithms. In addition, using a sufficiently large array of illumination sources mounted on eyewear or headwear may ensure that, during movement of the eye throughout its physiological range, at least one glint is projected onto the corneal region of the eye where there is a relatively simpler geometry (compared to the rest of the eye) and known reflective properties to calculate glint angles projecting from the cornea within camera images. Further, similar to the use of multiple cameras in a "range-finder" mode described above, multiple illumination sources may be used to continuously measure the position the eyewear or headwear device relative to the surface of the eye. Placing at least some illumination sources directly in the normal line-of-sight of the device wearer may also allow the gaze vectors (i.e., visual axes) of the device wearer to be close to known reference vectors generated using glints, improving the accuracy of gaze tracking.

In addition, illumination sources affixed to eyewear or headwear move about with the device wearer. This ensures illumination of the eye region even during wide-ranging movements of the head. During such head movements, glints and even overall illumination can be lost from illumination sources mounted some distance away from the head.

Camera processing units and illumination control electronics may also be mounted on the eyewear or headwear device that contains illumination sources. This allows direct on/off and/or intensity control of illumination sources and camera control without the use of external control devices, communications protocols and/or extensive wiring.

The systems and methods of the present application may maintain accurate gaze tracking under a wide range of conditions including when there is significant movement of: 1) the head, 2) eyewear or headwear that contains cameras and illumination sources, and/or 3) the eyes of the device wearer.

Gaze tracking is the ability to continuously identify the locations and/or objects being viewed by an observer. Gaze tracking may be computed from a combination of eye tracking and head tracking relative to identified reference locations within our three-dimensional world. The systems and methods of the present application may utilize multiple illumination sources and/or multiple cameras mounted on eyewear or headwear to accurately track the locations of pupils and other structures of the eye relative to the locations of glints produced by illumination sources mounted on the eyewear or headwear. Although glints and associated illumination sources may be in the direct line-of-sight of the observer, the methods described herein which the gaze tracking process may be performed largely unnoticed by the device wearer.

More particularly, the present invention is directed to apparatus, systems, and methods for unobtrusively identifying the locations of glints and anatomical structures on the surface of the eye of the device wearer for eye monitoring, control and other applications. The device may be configured as a platform for robust eye tracking that may be used by a wide range of individuals with varying anatomies of the head, nose, and eye region. Multiple glints projected from different angles and/or individual glints viewed from multiple angles may be used to estimate the positions of illuminations sources and cameras relative to the surface of the eye. The systems and methods herein may substantially continuously monitor the position of the eyewear or headwear that contains illumination sources and eye tracking cameras.

An increase in the resolution and/or pointing accuracy of a gaze tracking device may have a large number of beneficial consequences in a wide range of applications such as medical diagnostics, advertising, human factors, computer gaming, safety, rehabilitation engineering, and/or the control of a computer cursor (i.e., replacing or augmenting the operation of a computer mouse).

Thus, the apparatus, systems, and methods herein may provide an improved (i.e., high-resolution and robust) gaze tracking method and system for various applications.

In an exemplary embodiment, a method is provided that includes using multiple illumination sources that are affixed to eyewear or headwear to fully illumination substantially all regions around an eye. A single or small number of illumination sources may not provide adequate illumination for accurate eye tracking because of multiple curved surfaces in the region of the eye and anatomical structures (e.g., eyelids, eyelashes) that can block illumination. Illumination of the region of the eye with an array of illumination sources may allow for the production of multiple reference glints throughout the surface of the eye and/or more uniform illumination of curves surfaces, e.g., avoiding the generation of shadows and/or other lighting effects that may degrade machine vision techniques.

Similarly, the use of multiple cameras affixed to eyewear or headwear may also compensate for the complex geometry in the region of the eye. Images gathered from more than a single camera may be used to overcome structures (e.g., eyelids, eyelashes) that may block the visual field of a camera during eye tracking. In addition, the geometric distortion produced by objects (e.g., pupil, iris) that move about in a three-dimensional world when imaged by a camera that collects only two-dimensional images may lead to ambiguities in interpretation. This issue is particularly important when a camera is close (i.e., within three centimeters (3 cm)) to movements and those movements involve the rotation of an eyeball about a small radius (i.e., less than 1.5 centimeters (1.5 cm)). Both of these conditions may exist when unobtrusive cameras are mounted on eyewear or headwear. The use of images from multiple cameras mounted on eyewear or headwear and directed toward the eye from different angles may be used to substantially continuously track and/or reconstruct complex three-dimensional eye movements.

In accordance with one embodiment, each illumination source within an array of illumination sources may produce a glint on the surface of the eye that may be used as the starting location to generate a vector that passes from the glint through the location of the illumination source. The location of the illumination source is known relative to other illumination sources and cameras on the eyewear or headwear. By performing similar calculations using each illumination element in the array, an array of known vectors may be computed with known starting locations (i.e., glints) over the surface of the eye. Gaze tracking vectors, which use pupil position information projected from the surface of the eye, may then be expressed relative to these nearby known vectors, increasing the accuracy of gaze tracking.

In accordance with another embodiment, multiple illumination sources and/or multiple cameras may be used to calculate distances between the device and glints on the surface of the eye. These distances may be computed as distinct computational operations in gaze tracking processes, or measurements may be embedded within overall calculations of gaze tracking vectors. In either case, the exact positions of illumination sources and eye tracking cameras relative to the surface of the eye influence gaze tracking accuracy, especially over the short distances (i.e., less than three centimeters (3 cm)) associated with mounted structures on eyewear or headwear. Substantially continuously incorporating these distance measurements in gaze tracking calculations may eliminate the effects of this variability from user to user, and during sustained use when the eyewear or headwear may move about.

In accordance with another embodiment, illumination sources may be positioned in the direction normally used to view objects in the environment of the device wearer. This includes embedding illumination sources in the region normally occupied by lenses in typical eyeglasses or headwear. These illumination sources may be highly effective in illuminating the pupil, cornea, and/or surrounding regions during normal observational activities by the device wearer. In addition, glints generated by illumination sources embedded in lenses (or simple transparent material if the function of a corrective lens is not required) may be used to generate known vectors that are in close proximity to gaze-tracking vectors, increasing the accuracy of gaze-tracking.

In accordance with another embodiment, systems and methods are provided in which illumination sources utilize light that is invisible to the device wearer. Generally, wavelengths in the near infrared region of the electromagnetic spectrum are invisible to device wearers; yet overall illumination and glints produced by these illumination sources may be detected by solid state cameras that are affixed to the eyewear or headwear. Once again, the use of illumination that is invisible to the eye may support the overall unobtrusive nature of the eyewear or headwear device.

In accordance with yet another embodiment, systems and methods are provided in which illumination sources located in the lens region of eyewear or headwear are essentially invisible to the device wearer. This may be achieved using a number of strategies. The essential components of light-emitting diodes and other solid state devices that emit light are tiny. This principle may be used in display devices powered by LEDs and OLEDS where pixel sizes less than 0.2 millimeter are commercially available within laptop computers. LED sources with 0.01 millimeter dimensions per side are available for specialty applications. Thus, the semiconductor materials that make up an illuminating LED may be made to appear, at most, as a tiny speck. Furthermore, light used to illuminate the eye is invisible, e.g., in the near infrared range, from about 800 to 2500 nanometers in wavelength. Thus, the device wearer may not perceive the electromagnetic radiation emitted by the illumination source. On the other hand, CMOS cameras, in particular, are capable of detecting electromagnetic radiation in the near infrared spectrum that is not visible to the human eye. CMOS cameras are also particularly well suited in applications where low power and miniaturization are required.

Added to these factors, conductive pathways used to power illumination sources may be made essentially transparent. Transparent conducting films are well known in the manufacture of devices, such as solar cells and switchable glass (also known as smart glass used to construct windows). The most common material used in transparent conducting pathways is indium tin oxide (ITO). Less expensive alternatives such as aluminum-doped zinc oxide and indium-doped cadmium oxide represent additional examples of materials that may be used for transparent conducting pathways.

In summary, illumination sources may be largely invisible to the device wearer because: 1) the illumination sources may generate light at wavelengths that are invisible to the human eye, 2) the dimensions of solid state illumination sources may be tiny (approaching the resolution limit of light), 3) conductive pathways may be made that are essentially transparent, and/or 4) illumination sources may be close to the eye (approximately two centimeters (2 cm) away using a typical set of eyeglass frames) at a distance that is substantially less than the focal distance of most individuals. Thus, any light that might be reflected off of these tiny structures may be perceived as an out-of-focus background and not distracting to the device wearer. This may result in a substantially unobstructed view, supporting the overall unobtrusive nature of the eyewear or headwear device.

In accordance with yet another embodiment, systems and methods are provided in which illumination originating in the lens region of eyewear or headwear may be produced by small reflective surfaces embedded within each lens. Light may be generated by illumination sources that are placed around the edges of the lens and directed at the reflective surfaces. The reflective surfaces, in turn, may direct this light toward the eye. This configuration may eliminate the placement of illumination devices and conductive pathways to power those devices from the visual pathway of the observer, supporting the unobtrusiveness of the device.

In accordance with still another embodiment, systems and methods are provided that control the intensity of illumination sources that produce overall illumination and glint reference points on the surface of the eye. By controlling the timing of illumination relative to the timing of video image acquisition, it is possible to acquire images with and without illumination of reference glints. Subtracting images with illumination turned on, from images with illumination turned off, provides one (of several exemplary) strategies to isolate glints within images from eye tracking camera(s). Furthermore, if a single illumination source is turned on within a multiple illumination source system, then it may be easier to determine both the exact center location of the glint (i.e., compared to images that contain multiple glints) and associate a particular glint location with a specific illumination source.

Optionally, a processing unit may be coupled to one or more scene cameras directed substantially away from the eyes at the environment of the device wearer, and cameras for receiving images of the region of the eye, for example, to monitor the locations of glints and the edges of a pupil. The processing unit and scene-tracking processing unit may be one or more separate processors, or may be a single processor and/or include illumination controllers.

The use of multiple eye-tracking cameras directed at a single eye may produce multiple or redundant measurements of reference locations (e.g., glints, pupil edges, eyelids) in the region of an eye. When this situation occurs, processing unit(s) may take into account other factors that influence tracking accuracy. For example, if images of reference locations are closest to the center of the field-of-view of one camera, then it may be assumed that eye-tracking and subsequent gaze-tracking calculations based on measurements from that camera are more accurate than calculations based on measurements from other cameras where identified locations may be closer to the edges of camera images. Alternatively, when measurements of reference locations are near edges in all camera images, then ultimate determinations of reference locations may be computed as averages of locations computed using images from different cameras. This approach may take into account overlapping fields-of-view from adjacent cameras where spatial distortions near the edge of images from one camera may be opposite those measured by an adjacent camera. The averaging process may result in a cancellation of such distortions. Alternatively or in addition, if there are known distortions such as spherical aberration (produced to some degree by most lenses) or curvature of the eyeball in particular regions of camera images, then either corrective spatial mapping functions may be applied and/or measurements may be weighted prior to averaging. Such approaches or combinations of approaches will be appreciated by those of ordinary skill in the art.

In another embodiment, an illumination controller may be configured for amplitude modulation of at least one of the current and the voltage to the light source to provide desired brightness levels in the respective regions of eye-tracking camera images. This is generally referred to as "amplitude modulation." In another embodiment, the duration or "dwell time" of a controlling voltage or current may be modified to control light intensity. This is generally referred to as "pulse-width modulation." Optionally, it is also possible to use both schemes simultaneously.

In any of these examples, illumination, reference location tracking, eye tracking, and gaze tracking may be operated substantially continuously or intermittently. For example, illumination sources may be deactivated when the eye-tracking camera is inoperative. This may include times between acquiring camera images. Processors, cameras, and/or illumination may also be deactivated when not in use to conserve power. Illumination sources and/or other electronics may also be reduced in power or turned off for increased safety.

In an exemplary embodiment, the system may include an eyewear or headwear frame, a scene camera directed substantially away from the observer to identify reference locations, a scene processing unit coupled to the scene camera, at least one eye-tracking camera directed at an eye, one or more illumination sources directed at the eye, and a processing unit (same as or different than the scene processing unit) coupled to the eye tracking camera. Machine vision techniques may be used within the eye-tracking processing unit to determine the locations of glints and eye reference locations. Vectors produced by glint locations and associate illumination sources, along with eye reference locations identified within the eye-tracking processing unit, may then be used in gaze tracking calculations.

In accordance with another embodiment, a system is provided for determining gaze-tracking locations that includes a device configured to be worn on a wearer's head; one or more illumination sources mounted on the device within a field of view of an eye of a wearer wearing the device and oriented to illuminate the eye, the one or more illumination sources configured to minimize interference with the wearer's vision within the field of view; an eye-tracking camera mounted on the device and positioned for viewing the eye; and a processor coupled to the eye-tracking camera for analyzing images of the eye acquired by the eye-tracking camera to identify one or more glints reflected off the eye from the one or more illumination sources and identify the location of features of the eye relative to the one or more glints to determine locations being viewed by the wearer.

In accordance with yet another embodiment, a system is provided for determining gaze-tracking locations that includes a device configured to be worn on a wearer's head; one or more illumination sources mounted on the device oriented to illuminate an eye of the wearer; and a plurality of eye-tracking cameras mounted on the device and positioned for viewing the eye. A processor is coupled to the eye-tracking cameras for analyzing images of the eye acquired by the eye-tracking cameras to identify one or more glints reflected off the eye from the one or more illumination sources and identify the location of features of the eye relative to the one or more glints to determine locations being viewed by the wearer, wherein the eye-tracking cameras are sufficiently spaced apart from one another such that the eye's pupil appears in eye-tracking camera images from at least one of the eye-tracking cameras when the eye moves through its complete normal range of motion.

In accordance with still another embodiment, a system is provided for determining gaze-tracking locations that includes a device configured to be worn on a wearer's head, the device comprising a lens disposed in front of an eye of the wearer eye when the device is worn; a scene camera mounted on the device and positioned for viewing reference locations in the environment of the wearer; and a plurality of illumination sources mounted on the lens for illuminating the eye of the wearer; a plurality of eye-tracking cameras mounted on the device and positioned for viewing the eye. A processor is coupled to the scene camera and eye-tracking cameras for analyzing images therefrom that uses scene reference locations from scene camera images and eye-tracking locations from eye-tracking camera images to determine locations being viewed by the wearer.

In accordance with yet another embodiment, a method is provided for gaze tracking that includes placing a device on a wearer's head, the device comprising one or more illumination sources and a plurality of eye-tracking cameras oriented towards an eye of the wearer, the eye-tracking cameras positioned at different locations on the device to provide overlapping fields-of-view of the eye; and analyzing images of the eye acquired by the eye-tracking cameras to identify one or more glints reflected off the eye from the one or more illumination sources and identify the location of the features of the eye relative to the one or more glints to determine locations being viewed by the wearer.

In accordance with still another embodiment, a method is provided for gaze tracking that includes placing a device on a wearer's head, the device comprising a plurality of illumination sources and an eye-tracking camera oriented towards an eye of the wearer, the illumination sources disposed within a field of view of the wearer and configured to minimize interference with the wearer's vision within the field of view; and analyzing images of the eye acquired by the eye-tracking cameras to identify one or more glints reflected off the eye from one or more of the illumination sources and identify the location of the features of the eye relative to the one or more glints to determine locations being viewed by the wearer.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 3 also illustrates different examples of wiring configurations to power illumination sources mounted within the lens region of the eyeglasses.

DETAILED DESCRIPTION OF THE EXEMPLARY EMBODIMENTS

Figure 1:
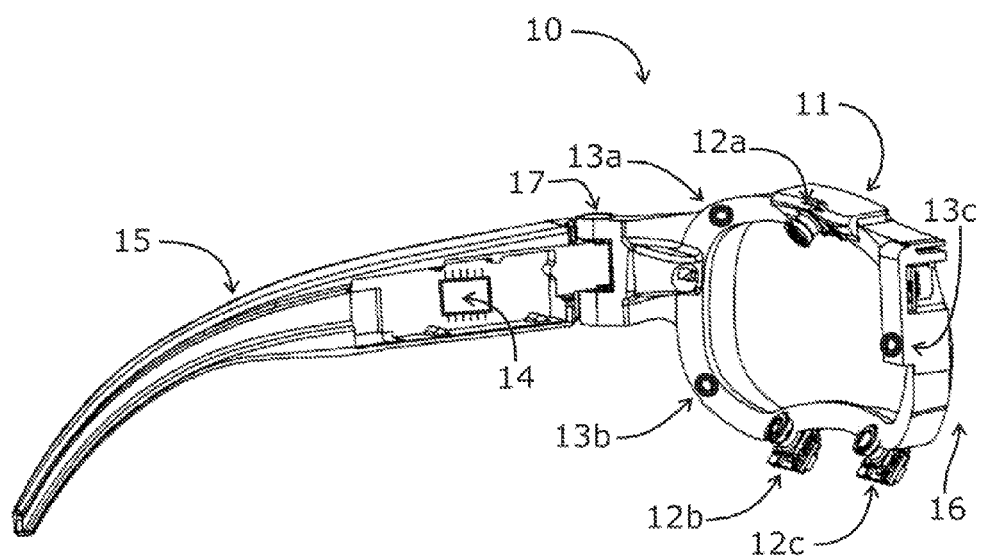
FIG. 1 is cut-away view of an exemplary embodiment of a system that includes a pair of eyeglasses including multiple cameras and multiple illumination sources mounted on the eyeglass frame.

Turning to the drawings, FIG. 1 shows an exemplary embodiment of a system 10 including an eyeglass frame 11 with three eye-tracking cameras 12a, 12b, 12c directed at the left eye (not shown) of the device wearer. Also directed at the left eye of the device wearer are three illumination sources 13a, 13b, 13c, in this case, mounted on the eyeglasses frame 11. Images collected by the eye-tracking cameras 12a, 12b, 12c are sent to a processing unit 14. In this exemplary embodiment, the processing unit is mounted within the left stem 15 of the frame 11 and coupled to the cameras 12a, 12b, 12c. Optionally, to distribute weight more evenly within the eyeglass frame 11, a power source (e.g., battery, not shown) and/or other electronics may be encased in the stem of the eyeglass frame 11 opposite that containing the processing unit 14 (not shown).

The processing unit 14 may also include memory for storing image signals from the camera(s) 12a, 12b, 12c, digital filters for editing and/or processing the image signals, and the like. Optionally, the eyeglass frame 11 and/or processing unit 14 may include one or more, transceivers, transmitters, and/or receivers (not shown) for transmitting data, receiving instructions, and the like. In addition or alternatively, processing may include components that are remote from the frame 11 and/or the processing unit 14, similar to embodiments disclosed in the references incorporated by reference elsewhere herein. For example, the system 10 may include one or more transmitters, receivers, processors, and/or displays (not shown) at one or more remote locations from the processing unit 14 and/or frame 11, e.g., in the same room, at a nearby monitoring station, or at a more distant locations. Such displays may include views generated by the eye-tracking cameras 12a, 12b, 12c and/or one or more scene cameras (not shown) on the frame 11.

Eye-tracking cameras 12a, 12b, 12c may be directed toward the head in order to track the locations of pupils, eyelids, irises, glints, and/or other reference points in the region of the eye(s) being imaged. In an exemplary embodiment, eye-tracking cameras 12a, 12b, 12c may include charge-coupled device (CCD), complementary metal-oxide-semiconductor (CMOS), or other detectors that include an active area, e.g., including a rectangular or other array of pixels, for capturing images and/or generating video signals representing the images. The active area of each of the cameras 12a, 12b, 12c may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

Figure 5:
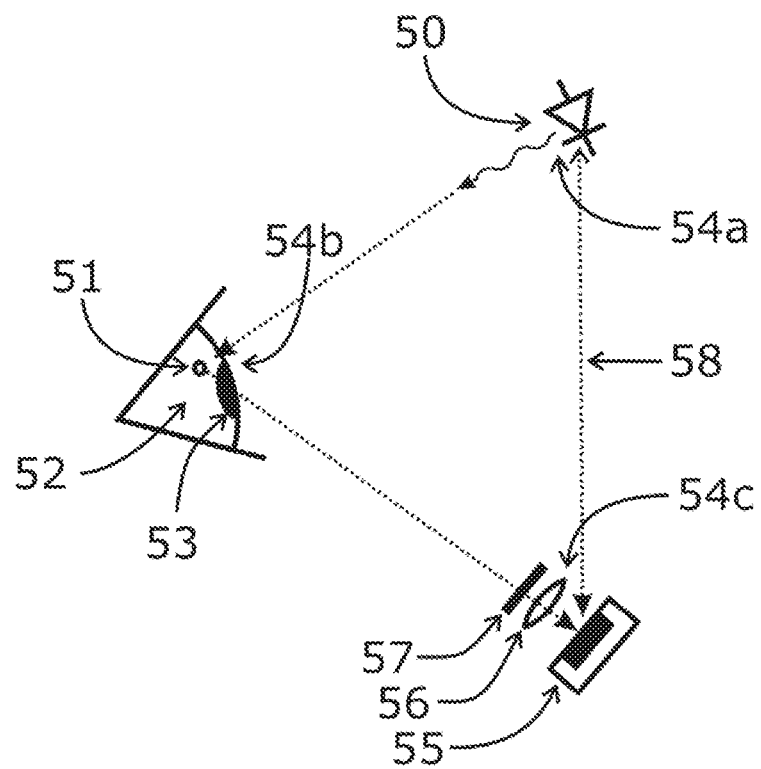
FIG. 5 is a schematic illustrating exemplary geometric components of calculations in which the distance between the surface of an eyeball and a camera may be substantially continuously computed using triangulation.

In addition, the cameras 12a, 12b, 12c may include one or more filters, lenses, and the like (e.g., filter 57 and lens 56 as illustrated in FIG. 5), if desired, e.g., to filter undesired intensities and/or wavelengths of light, focus images on the active area, and the like. Optionally, the lenses may also be configured to stretch or compress regions of the field-of-view in order to compensate, at least to some degree, for the nearby three-dimensional curvature of the eye and surrounding structures.

Multiple cameras may be positioned at different locations on the frame 11 to facilitate substantially continuously monitoring movements of the three-dimensional structures of the eye in all directions. For example, in the embodiment shown in FIG. 1, cameras 12b and 12c are positioned particularly well to track eye movements as they occur in the horizontal axis (i.e., assuming a normal, upright head position). Similarly, accurate eye tracking data may be gathered using camera 12a during upward movements of the eye (e.g., relative to a "straight-ahead" orientation), whereas cameras 12b and 12c are well-positioned to monitor reference locations on the surface of the eye when looking downward.

In the embodiment illustrated in FIG. 1, a single processing unit 14 is used to acquire images from the various cameras within the system 10. Processing and/or other control electronics may include a single device or multiple devices, such as a micro-controller, single or multi-core central processing unit (CPU), field-programmable gate array (FPGA) or application specific integrated circuit (ASIC).

Other locations to house electronic processing and control elements include above the nose region 16 of the eyeglass frame 11, within the right stem (not shown) of the frame 11, within an external compartment (e.g., fastened to the device wearer's belt or head band) electrically tethered to and/or wirelessly communicating with the eyewear or headwear, or elsewhere within the frame of the system 10. Alternatively, electronically processing and control elements may be distributed at different locations within the system 10, for example, to more evenly distribute weight, dissipate heat, shorten the lengths of cables, and/or reduce power consumption.

In the embodiment illustrated in FIG. 1, three illumination sources 13a, 13b, 13c are affixed to the solid frame of the eyewear or headwear. In an exemplary embodiment, illumination sources 13a, 13b, 13c may include light-emitting diodes (LEDs), organic LEDs (OLEDs), laser LEDs, or other devices that convert electrical energy into photons. Each illumination source 13a, 13b, 13c may be used to illuminate the eye to acquire images using any of the cameras 12a, 12b, 12c and/or to produce reference glints for measurement purposes to improve gaze-tracking accuracy. In an exemplary embodiment, each light source 13a, 13b, 13c may be configured for emitting a relatively narrow or wide bandwidth of the light (e.g., infrared light at one or more wavelengths between about 640-700 nanometers). Optionally, one or more light sources 13a, 13b, 13c may include lenses, filters, diffusers, reflectors, and/or other features (not shown), for example, to facilitate and/or control the uniformity of light projected toward the eye. Illumination sources may be activated (i.e., powered) individually, all together, or in any combination.

Cable(s) embedded within the eyewear or headwear frame 11 may include individual cables or sets of wires, including so-called "flex strips," coupled to cameras 12a, 12b, 12c batteries, light sources 13a, 13b, 13c, and/or other components on the frame 11 and/or to the processing unit(s) 14. For example, the cable(s) should be sufficiently flexible to traverse hinge regions 17 within the eyewear or headwear device, e.g., to avoid breakage even when the hinge 17 is flexed through its extreme range of motion.

Figure 2:
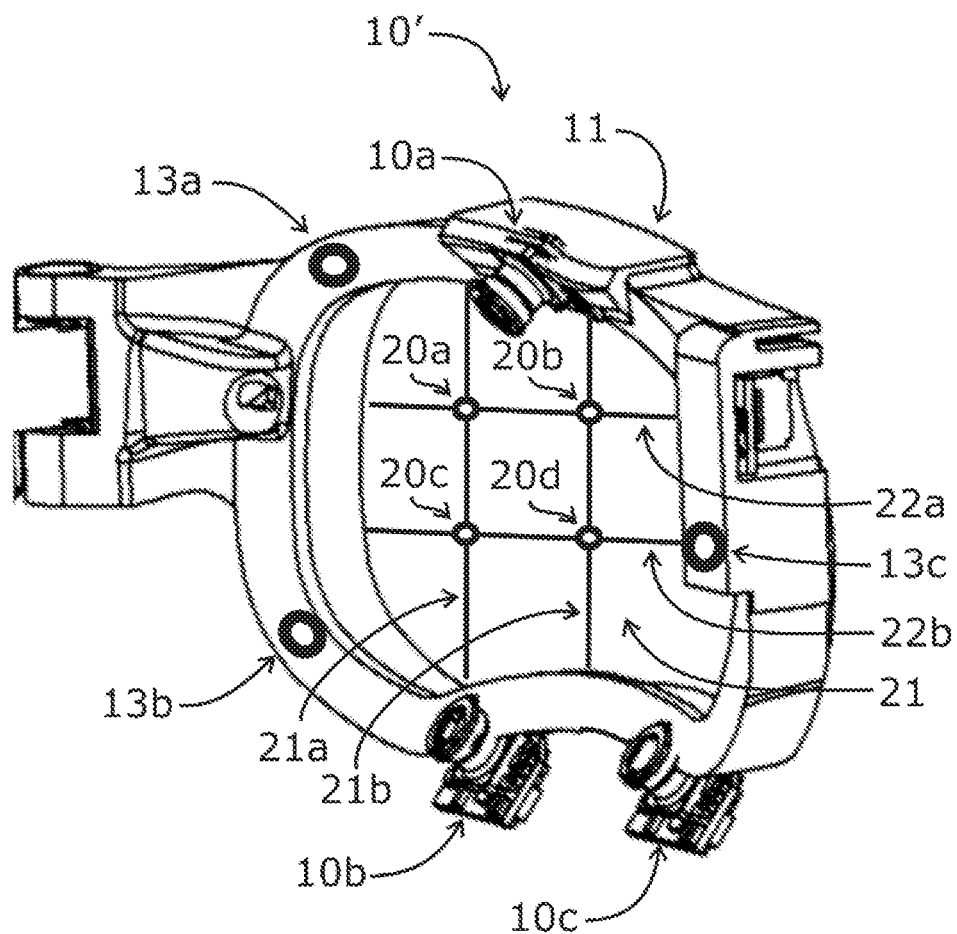
FIG. 2 is a close-up view of the system of FIG. 1 in which illumination sources are mounted both on the frame as well as within the lens region through which the device wearer views the environment.

FIG. 2 is a close-up view of the lens region of the eyeglass frame 11 of a system 10' similar to that shown in FIG. 1. In this case, additional illumination sources 20a, 20b, 20c, 20d are positioned in the region of the eyeglass frame 11 normally occupied by a lens 21. If the device wearer requires optical correction to aid visualization, then appropriate lenses may be constructed and inserted using processes well-known in the field of optometry. If visual correction is not required by the device wearer, then the lens region may simply be occupied by a flat piece of glass or optically clear plastic to support the line-of-sight illumination sources 20a, 20b, 20c, 20d. Thus, as used herein, "lens" may refer to a corrective lens, i.e., that refracts light or otherwise corrects the wearer's vision through the lens, or to a substantially flat, curved, or other panel of substantially clear material that does not substantially refract light or otherwise modify the view of a wearer of the frame 11 looking through the lens.

Figure 7A:
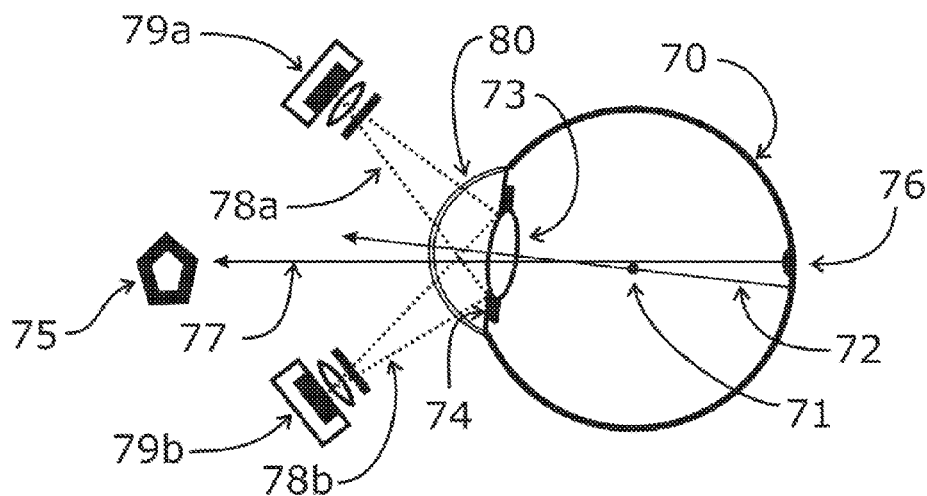
FIGS. 7A and 7B are schematics illustrating how the pivoting of an eyeball may obscure the view of a single camera, limiting the ability to make accurate gaze tracking measurements, whereas multiple cameras may make accurate eye tracking measurements throughout a full range of eye movements.
Figure 7B:
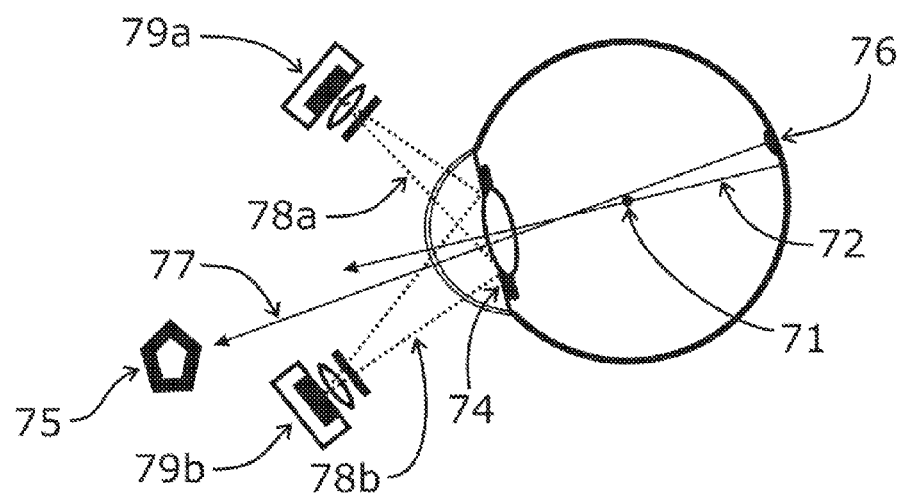

The additional or alternative illumination sources 20a, 20b, 20c, 20d mounted within the lens regions of the eyeglass frame 11 may be used to augment or replace illumination of the eye provided by sources 13a, 13b, 13c mounted on the eyeglass frame 11. Sources 20a, 20b, 20c, 20d mounted within the line-of-sight of the device wearer may be generally better able to substantially uniformly illuminate critical regions (i.e., in and around the cornea, e.g., as shown in FIGS. 7A and 7B) of the eye during normal visual activities. In addition, these same illumination sources 20a, 20b, 20c, 20d may produce glints with associated pointing vectors that are much closer to the normal line-of-sight of the eye (see, e.g., FIGS. 7A and 7B) during visualization (i.e., compared to sources 13a, 13b, 13c mounted off-axes on the eyeglass frame 11).

Gaze vectors may be computed more accurately if they are calculated relative to glints that are: 1) positioned on or near the pupil within the cornea, and/or 2) created by illumination sources that point in approximately the same direction as the line-of-sight or visual axis of the observer. Thus, gaze vectors computed using glints on the surface of the eye generated by illumination sources 20a, 20b, 20c, 20d within the lens generally have a higher degree of pointing accuracy, e.g., than sources located elsewhere on the frame 11, such as the sources 13a, 13b, 13c shown in FIGS. 1 and 2. As described elsewhere, illumination sources 20a, 20b, 20c, 20d may be constructed so as not to interfere with the normal vision of the device wearer.

At least two conductive pathways may be provided to power one or more of the illumination sources 20a, 20b, 20c, 20d. FIG. 2 illustrates one wiring pattern that permits either individual or group control of all illumination sources 20a, 20b, 20c, 20d. As shown, conductive pathways may include vertical 21a, 21b and horizontal 22a, 22b conductors. By applying a voltage to a vertical conductive pathway 21a or 21b relative to a horizontal conductive pathway 22a or 22b, a potential difference (i.e., voltage) is available at the location of intersection of the two activated conductive pathways. This potential difference may be used to power an individual illumination source. All other conductive pathways not associated with the desired illumination source may be placed in a high impedance (i.e., non-conducting) mode in order not to power additional illumination sources or draw unwanted current. The vertical 21a, 21b and horizontal 22a, 22b conductive pathways may be insulated from each other (except through the illumination source elements themselves) at points of intersection.

With further reference to the embodiment shown in FIG. 2, if there is a need for all illumination elements to be activated, a potential difference may be applied between all vertical 21a, 21b and horizontal 22a, 22b conductive pathways. Similarly, a column of illumination sources may be activated by applying a potential difference between a vertical conductive pathway 21a or 21b and all horizontal pathways 22a and 22b; or a row of illumination sources may be activated by applying a potential difference between a horizontal conductive pathway 22a or 22b and all vertical pathways 21a and 21b. As described elsewhere in greater detail, the conductive pathways may be made substantially transparent and/or unobtrusive by being thin and/or made of materials, such as ITO, that are transparent.

Figure 3:
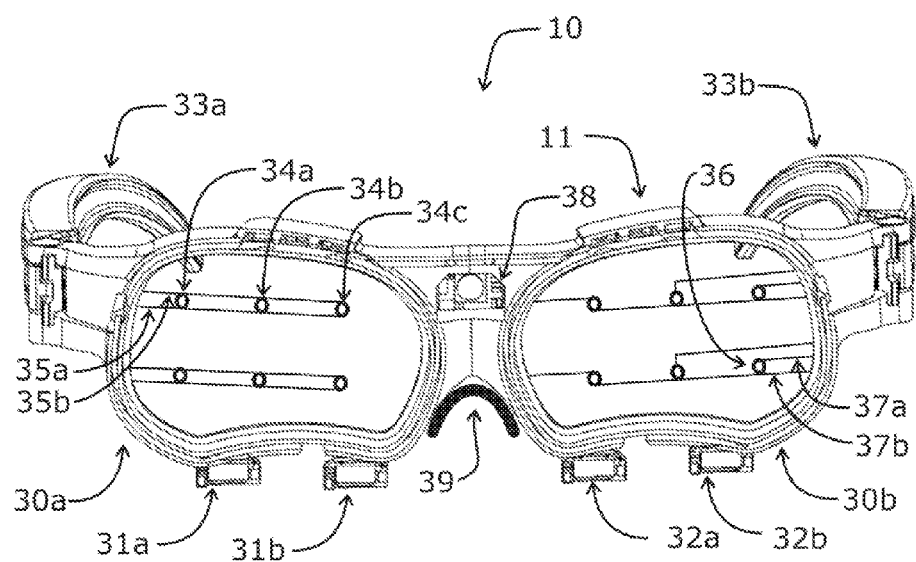
FIG. 3 is a front view of another embodiment of an eyewear system including multiple cameras mounted on an eyeglass frame and multiple illumination sources mounted within the lens region of the eyeglass frame.

FIG. 3 shows an embodiment of a gaze-tracking system 10" including one or more components embedded within an eyewear platform 11 as viewed from the front (i.e., looking toward the device wearer). In this case, the eyewear platform 11 is instrumented to track both the right eye using components mounted to the right eyeglasses frame 30a and the left eye using components mounted to the left eyeglasses frame 30b. From the viewpoint of the system 10" of FIG. 3, the rear side of some of the cameras used to track the right eye 31a, 31b and left eye 32a, 32b may be seen. As described more fully elsewhere, processing and control electronics and/or power sources may optionally be embedded in one or both the right 33a and left stems 33b of the eyewear 11.

Also shown in FIG. 3 are two alternative (compared with FIG. 2) patterns of conductive pathways that may be provided on the eyewear 11 to power illumination sources that are located in the overall visual field of the device wearer. If control of individual illumination sources is not required, then the pattern of sources shown within the right eyeglasses frame 30a may be utilized. In this example, horizontal rows of illumination sources 34a, 34b, 34c may be activated simultaneously by applying a potential difference (i.e., voltage) across conductive pathways 35a and 35b. Any number of illumination sources (where three sources 34a, 34b, 34c are illustrated in FIG. 3) may be provided within each row using this parallel connection of devices to conductive pathways. In addition, any number of rows may be provided. Conductive pathways may, for example, be arranged in horizontal rows, as shown; vertical columns; radial patterns (not shown); and the like. A further advantage of these patterns (compared to those illustrated in FIG. 2) is the lack of a need to insulate conductive pathways at points of intersection, since there are no intersections. This may facilitate depositing conductive pathways on transparent glass or optically clear plastic lens surfaces.

The left eyeglass frame 30b illustrates yet another pattern of conductive pathways that may be used to activate illumination sources. In this case, illumination source 36 may be individually controlled by a potential difference applied across conductive pathways 37a and 37b. At least one separate conductive pathway is directed at each illumination source. If desired, one of the pathways that powers each illumination source, as illustrated by conductive pathway 37b, may be shared among several illumination sources. In the field of electronics, this is often referred to as a reference or ground pathway. An advantage of the pattern of conductive pathways shown in the left eyeglasses frame 30b is the ability to control individual illumination sources without any intersections of conductive pathways that would necessitate an insulating layer during construction to keep pathways electrically isolated.

The system 10″ shown in FIG. 3 also illustrates an example of the placement and use of an outward-pointing scene camera 38 that gathers images of the environment of the device wearer (which may also be provided on any of the other embodiments herein). Methods related to processing and applications of scene camera images including tracking reference locations within the environment of the device wearer are disclosed in embodiments disclosed in the references incorporated by reference elsewhere herein. Methods related to using scene camera images to measure responses and/or reaction times of movements of the eye and other structures within the head of the device wearer are also disclosed in the references incorporated by reference elsewhere herein.

As discussed next more fully, in association with FIGS. 5-7, the position of eyewear or headwear resting on the nose of the device wearer is a useful variable for ensuring gaze tracking accuracy. FIGS. 5-7 illustrate methods to measure distances between device components and the surface of the eye. In order to mitigate some of the variability in the size and/or position of the noses of individuals (relative to their eyes), an adjustable nose piece 39 may be incorporated within the frame of the eyewear or headwear 11, as shown in FIG. 3. Adjustability may be incorporated by using interchangeable nose piece inserts (not shown) as well as by flexing or otherwise adjusting the support structures and/or padding within and individual nose piece 39. In addition, eyewear or headwear frames of different sizes may be fitted to individuals, e.g., by providing various standard sizes and/or providing custom sizes for specific individuals.

Figure 4:
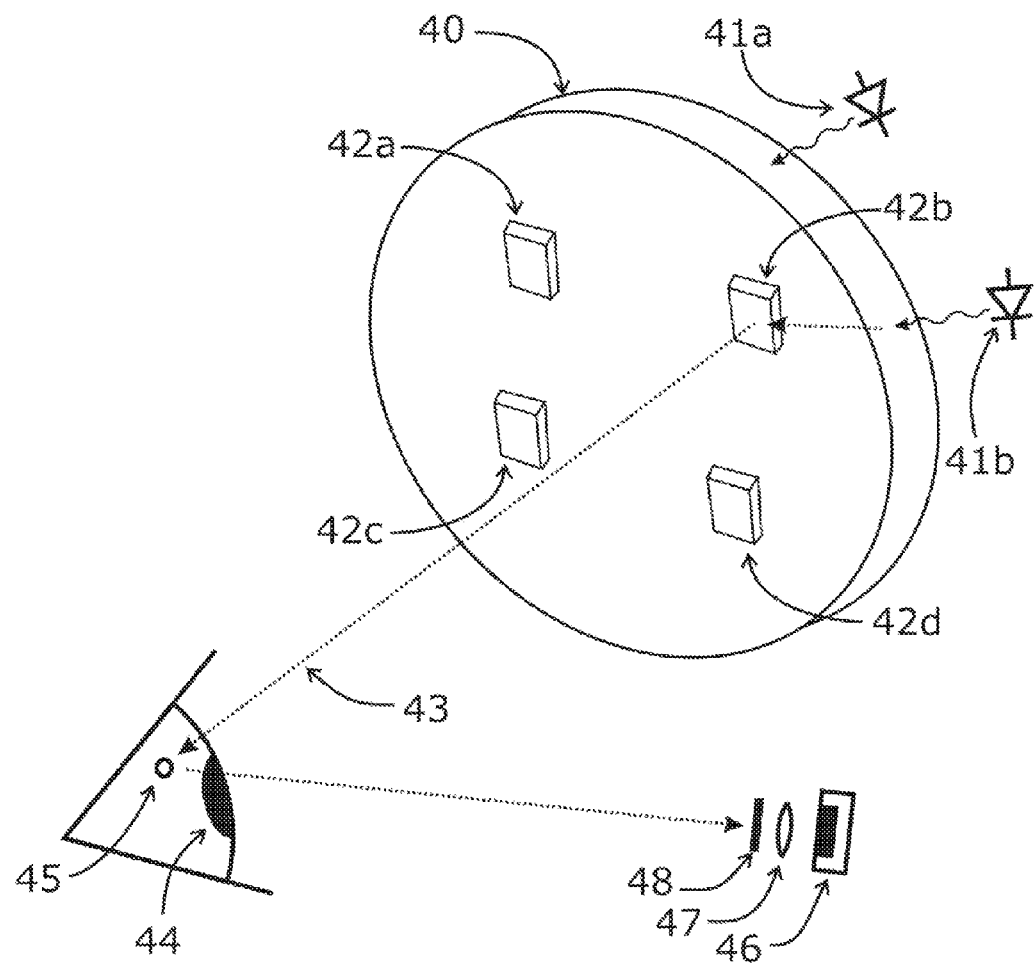
FIG. 4 is a close-up view of the lens region of an exemplary system where lighting is produced remotely and illumination of the eye occurs as a result of reflections from small reflective surfaces within the lens.

The embodiment shown in FIG. 4 illustrates another method to unobtrusively produce multiple point sources of illumination from within the lens 40 of an eyewear or headwear (not shown). In this case, lighting is produced remotely from the central region of the lens. For example, one or more light sources 41a, 41b (e.g., LEDs) may couple electromagnetic radiation along one or more sides of the lens 40 into the material comprising the lens (i.e., generally glass or clear plastic). The electromagnetic radiation propagates through the lens medium and is then reflected toward the eye by small reflective surfaces 42a, 42b, 42c, 42d provided at desired locations within the lens 40 (four shown substantially evenly spaced from one another, although fewer or more reflective surfaces may be provided, as desired). In the drawing shown in FIG. 4, the sizes of the reflective surfaces 42 are shown enlarged relative to the overall size of the lens in order to visualize structural features of the reflective surfaces 42. The use of remote sources of electromagnetic radiation and small, embedded reflective surfaces 42 to reflect infrared light (thereby completely eliminating conductive pathways in the lens region) may result in a line-of-sight illumination system that is substantially transparent to the device wearer.

With further reference to FIG. 4, the reflective surfaces may be constructed using a number of techniques that are well-known in the field of photolithography and semiconductor fabrication. Such methods may involve the use of etching or micro-machining to produce a surface that is angled such that electromagnetic radiation propagating through the lens is directed toward the eye 43. Etching or micro-machining processes may be directed from the back surface (i.e., closest to the eye) or the front surface (i.e. away from the eye) of the lens 40. A reflective material may then be deposited, e.g., using well-known vapor deposition, sputtering, and/or chemical precipitation techniques on the reflective surfaces 42a, 42b, 42c, 42d. Most commonly, a metal (e.g., silver, aluminum, and the like) may be used to generate reflective, mirrored surfaces.

Optionally, the volume that was removed by the etching or micro-machining process may be re-filled by a material that matches the refractive index of the lens material in order to avoid any further, unwanted refraction or reflections of the light that is directed toward the eye 43 and/or to keep dirt from accumulating in the small indentations 42a, 42b, 42c, 42d.

In some embodiments, it is not necessary to coat the reflective surface with a metal. Reflections may occur as long as there is an interface between two materials with differing refractive indices to light. Thus, the volume that was removed by etching or micro-machining may be re-filled with a material with a refractive index that is intentionally chosen to be different compared to the material that makes up the lens. This same principle may be used to reflect light within prisms (with contrasting refractive indices of glass versus air) and fiber optic transmission. By appropriate selections of refractive indices and/or thicknesses of coatings, the surfaces within the lens structure may be made partially or fully reflective.

With further reference to FIG. 4, light from the reflective surfaces 42 may be used both to illuminate the pupil 44 along with other structures of the eye for tracking purposes, and/or to produce reference glints 45 on the surface of the eye. The pupil 44 and glints 45 may be tracked by one or more eye-tracking cameras 46 (one shown) where, as described in more detail elsewhere, images are brought into focus on the sensing array of the camera(s) 46 by a miniature lens 47. Optionally, an optical notch filter 48 may also be used to substantially isolate light generated by light sources 41 and reflected at the surface of the eye while eliminating most environmental sources of light. Similar to using illumination sources directly embedded in the lens (e.g., as illustrated in FIGS. 3 and 4) reflective surfaces 42a, 42b, 42c, 42d in the line-of-vision of the device wearer may produce glints directly on the cornea, simplifying geometric considerations when calculating gaze tracking vectors. Gaze tracking vectors are also closer to reference vectors 43 calculated as a line that passes through glints and reflective surfaces 42, resulting in increased gaze tracking accuracy.

FIG. 5 illustrates some of the components of a "rangefinder" or triangulation method to estimate the position of one or more eye-tracking cameras (and thus, the eyewear or headwear device, not shown) relative to the surface of an eye. This measurement may contribute to the accuracy of gaze tracking calculations by taking into account facial variations in the anatomy of the head (particularly the size of the nose when using eyewear that rests on the bridge of the nose) and whether there is any dynamic movement of the eyewear or headwear as a result of slippage or rapid accelerations of the head during use.

In FIG. 5, an illumination source 50 (which may be any of the illumination sources and/or reflective surfaces described elsewhere herein) produces a glint 51 on the surface of the eye. The beam of the illumination source 50 may be positioned and directed in all three dimensions (illustrated as angle 54a) to maximize illumination (particularly glint production) in the central region of the eye. Accurate gaze tracking may be computed most readily when glints are within the cornea (see FIG. 7), on or near the pupil 53; although within images gathered by eye tracking cameras 55, glints 51 may occur on the sclera or white portion of the eye 52 and/or iris that surrounds the pupil (not shown in FIG. 5 for clarity).

With further reference to FIG. 5, images of the central region of the eye may be brought into focus on a camera 55 by a lens 56. In most applications, a notch (i.e., band-pass) optical filter 57 may be included in the (infrared) light pathway, allowing transmission of the wavelengths of light generated by the illumination source 50 and reflected off of the surface of the eye to reach the camera 55. All other wavelengths of light that generally come from the surrounding environment and may interfere with images of glints 51 and/or reflections off of the pupil 53 may be absorbed by the filter and do not reach the camera 55.

Glints 51 appear as intensely bright spots (often saturating some camera pixels) in images from the camera 55. Determining the central location of a glint is generally considered a relatively easy image-processing step where, for example, the average horizontal and vertical positions of all pixels that exceed a selected (i.e., threshold) intensity value may be computed. This method may produce sub-pixel spatial resolution of the location of bright glints in each dimension. Given the known orientation of each camera 55 mounted to eyewear or headwear, the measured location of each glint relative to the center of the field-of-view (i.e., relative to the center of camera images) is proportional to the angle 54c subtended by the glint and the center of the field-of-view of the camera 55.

Illumination sources 50 are targeted at the corneal region of the eye (see FIG. 7). Although the overall surface of the eye has a complex morphology, the corneal shape may be approximated as a portion of a sphere with a smooth surface. The angle of reflection 54b of the illumination source may then be modeled in a number of ways including (most simply, assuming specular reflection) that the angle of incidence is equal to the angle of reflection. In order to take into account more diffuse scattering of light, Lambert's cosine law may also be brought into equations.

Both the camera(s) 55 and illumination source(s) 50 may be substantially rigidly affixed to the eyewear or headwear. Thus, the three-dimensional orientation and separation distances 58 (in all three dimensions) between all camera(s) 55 and illumination source(s) 50 may be known. Knowing two angles and a separation distance 58 allows the calculation of all distances separating the light source 50, glint 51, and camera 55; and associated angles using well-known triangulation techniques. Similar approaches are used, for example, within range finder instruments, surveying methods, and when estimating distances to objects in space.

Figure 6A:
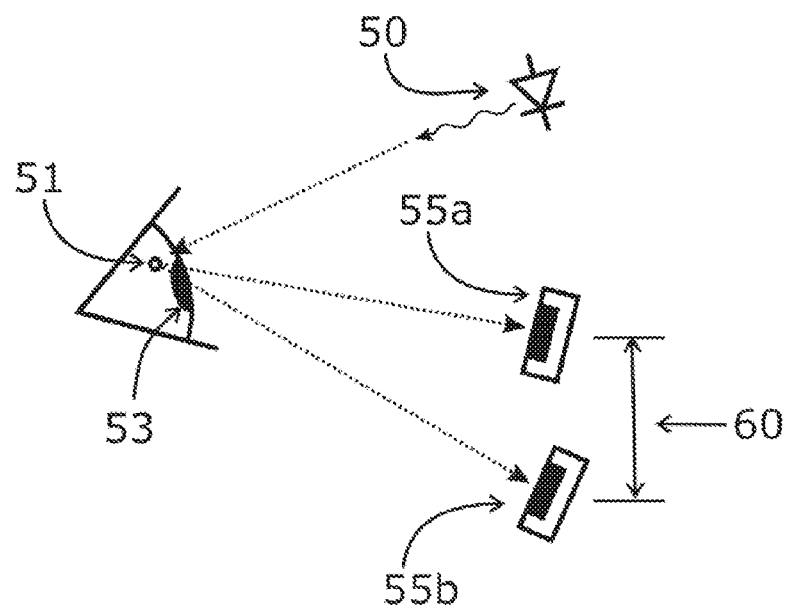
FIGS. 6A and 6B are schematics illustrating exemplary components used in calculations of distance to an eyeball surface measured with multiple cameras (FIG. 6A) and/or multiple illumination sources (FIG. 6B).
Figure 6B:
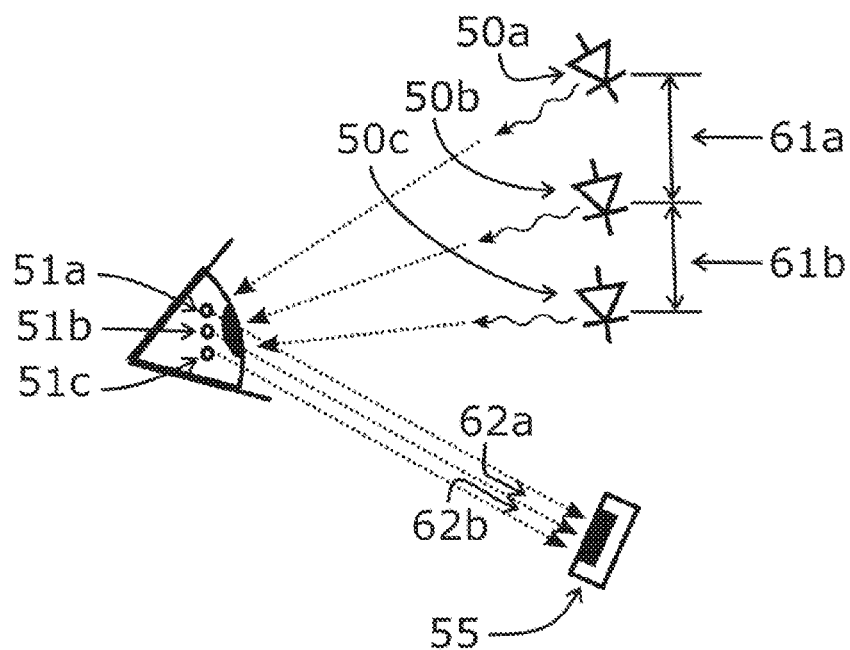

The embodiments shown in FIGS. 6A and 6B illustrate methods to further improve the accuracy of distance and/or angular measurements using multiple cameras (FIG. 6A) to image glints from different locations and/or multiple illumination sources to produce multiple glints (FIG. 6B). As mentioned in descriptions associated with FIG. 5, a degree of uncertainty arises as a result of micro-variations in the three-dimensional curvature of the eye surface as well as specular versus diffuse scattering of light off of the surface of the eye. By measuring two or more glints, uncertainty in measurements may be cancelled in gaze-tracking equations, resulting in an increase in the precision of position measurements in all three dimensions.

In FIG. 6A, a single illumination source 50 produces a single glint 51 on the surface of the eye. As previously mentioned, the most useful glints are those that are on or near the pupil 53 within the region of the cornea (see 80 in FIG. 7A). The position of the glint 51 is determined within images from two or more cameras 55a, 55b. Cameras are separated by known distances in all three dimensions (60 in the case of the separation distance between cameras 55a and 55b, shown in FIG. 6A). Viewing angles relative to a plane defined by the cameras and the light source are also known. By measuring differences in the locations of a glint 51 within images from multiple cameras 55a, 55b, distances between cameras 55a, 55b and the glint 51 on surface of the eye may be estimated using triangulation.

A similar approach may be used in the method illustrated in FIG. 6B except, in this case, multiple illumination sources 50a, 50b, 50c produce multiple glints 51a, 51b, 51c on the surface of the eye. Glints may be produced at the same time when multiple illumination sources 50a, 50b, 50c are activated. This technique adds complexity to the image processing algorithms where the locations of multiple glints with similar intensity values and shapes must be extracted from a single image.

By turning each illumination source on at selected times, it is alternatively possible to produce a series of images where it is necessary to determine the location of only a single glint, 50a or 50b or 50c, at a time. This leads to more easily implemented and reliable image processing methods to determine the location of individual glints (and its corresponding illumination source) within images.

The separation in the measured location of glints normalized by the actual separation of illumination sources is inversely proportional to the distance between the camera and the surface of the eye. For example, the separation 62a measured between glint 51a and 51b divided by the known separation 61a between illumination sources 50a and 50b is inversely proportional to the distance between the camera and the surface of the eye. Similarly, the separation 62b measured between glint 51b and 51c divided by the known separation 61b between illumination sources 50b and 50c is inversely proportional to the distance between the camera and the surface of the eye. Thus, an algorithm may be readily generated identifying the relationships between the illumination sources 50a, 50b, eye, and camera 55 to facilitate accurate gaze tracking of the eye in images acquired by the camera 55, as will be appreciated by those of ordinary skill in the art.

The embodiment shown in FIGS. 7A and 7B illustrate how multiple cameras directed to view the surface of the eye from multiple angles may improve the accuracy of gaze tracking, as well as the ability to substantially continuously track reference structures within the eye during normal movements of the eye. Eye movement may be approximated as rotation of the eyeball 70 about a central pivot point 71 that lies along the eye's optical axis 72. The optical axis generally runs through the center of the eye's lens 73 and is substantially perpendicular to the surfaces of the lens at its center.

Surrounding the lens is the iris 74 with unique microanatomical structures within every eye (including left and right eyes of an individual) and is responsible for controlling the size of the opening in front of the lens 73, and thus, the amount of light that passes through the lens 73. External to the iris 74 and lens 73 is the semi-spherically shaped cornea 80. Because of the smooth corneal surface and because the line-of-sight or visual axis 77 must pass through the cornea 80, the corneal surface is a prime target for generating reference glints (see FIGS. 4-6) for accurate gaze tracking measurements.

Under most lighting conditions, the region where light enters the lens appears dark and is referred to as the pupil. One example of a situation when a pupil does not appear dark is the so-called "red eye" effect that typically occurs when a person is photographed from some distance using a flash light source and camera detector that are nearly parallel in light paths. The current invention does not generally produce this effect since cameras and light sources are well separated (e.g., as shown in FIG. 1).

In FIGS. 7A and 7B, dashed lines 78a, 78b have been inserted to indicate the edges of a dark pupil as observed by each camera assembly 79a, 79b. Many image processing approaches use the edges of the pupil identified by the contrast between the dark pupil region and the iris 74 as identifiable locations that are then used as foundational inputs for gaze-tracking calculations. Alternatively, the center of a pupil may, for example, be identified by calculating the average position of a cluster of dark pixels that are less than (i.e., darker than) a threshold light intensity value in camera images.

It is well-known in the field of ophthalmology (i.e., the study of the physiology of the eye) that the center of focus when viewing an object 74 is not along the optical axis 72. Rather the fovea (i.e., fovea centralis, 76), an approximately one millimeter (1 mm) diameter structure (in humans) located in the center of the macula region of the retina, is responsible for sharp vision. Thus, the visual axis 77, a line between the fovea 76 and the object being viewed 75, most often does not intersect the lens 73 at its physical center. In other words, the center of the pupil of the observer usually does not precisely track the center of the target object 75 being viewed.

Further compounding the non-colinear alignment of the visual and optical axis is the three-dimensional geometry of the eye's surface and rotation movements of the eyeball. Unless a camera 79a or 79b is positioned exactly along the optical axis (where images of a pupil appear circular), camera images of pupil edges appear as approximately elliptical. Cameras 79a or 79b located further off-axis record pupil images that are increasingly elongated (i.e., less circular). This elongation may exaggerate the separation between the optical 72 and visual 77 axes.

In FIG. 7A, both camera assemblies 79a, 79b may readily view the edges of the pupil 78a, 78b where both the optical 72 and visual 77 axes appear roughly (although not exactly) near the center of the image of the pupil. However, following a modest rotation of the eye as illustrated in FIG. 7B, images of the pupil as observed by camera 79a are highly elongated. Furthermore, the visual axis 77 is well away from the middle of the pupil edges (i.e., well away from the middle of the field-of-view formed by dashed lines 78a). In fact, the visual axis 77 appears close to the edge of the iris in images collected by camera 79a.

Further rotation of the eye may cause a complete loss of the ability of camera assembly 79a to track the pupil. Compounding this issue in some individuals are anatomical structures such as swollen or partially closed eyelids and/or "puffy" lower parts of the eye that may further obscure substantially continuous tracking of the eye. The near-field location of cameras mounted on eyewear or headwear (versus cameras mounted further away, for example, on the dashboard of a car or near the display monitor of a computer) exacerbates this issue. However, multiple cameras (e.g., 79a and 79b in FIG. 7B) strategically placed to capture the full range of motions of the eye in all dimensions may provide substantially continuous and/or accurate monitoring of pupil movements throughout the full, physiological range of motions in addition to being less obscured by other anatomical structures of the eye and face.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented methods and/or processes as a particular sequence of steps. However, to the extent that the methods or processes do not rely on the particular order of steps set forth herein, the methods or processes should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for determining gaze-tracking locations, comprising:
    a device configured to be worn on a wearer's head;
    one or more illumination sources mounted on the device within a field of view of an eye of a wearer wearing the device and oriented to illuminate the eye, the one or more illumination sources configured to minimize interference with the wearer's vision within the field of view;
    an eye-tracking camera mounted on the device and positioned for viewing the eye; and
    a processor coupled to the eye-tracking camera for analyzing images of the eye acquired by the eye-tracking camera to identify one or more glints reflected off the eye from the one or more illumination sources and identify the location of features of the eye relative to the one or more glints to determine locations being viewed by the wearer;
    further comprising one or more additional eye-tracking cameras mounted on the device and positioned for viewing the eye, the processor coupled to the one or more additional eye-tracking cameras to track locations of the eye from different viewing angles, wherein the eye-tracking cameras are sufficiently spaced apart from one another such that the features of the eye appear in eye-tracking camera images from at least one of the eye-tracking cameras when the eye moves through its complete normal range of motion.

2. The system of claim 1, wherein the one or more illumination sources comprise one of a LED and OLED emitter.

3. The system of claim 1, wherein the device comprises a lens mounted thereto within the line of sight of the wearer, and wherein the one or more illumination sources comprise a plurality of light sources provided on the lens to illuminate the eye.

4. The system of claim 1, wherein the illumination source comprises a plurality of reflective surfaces embedded in a lens mounted to the device in front of the wearer's eye, and one or more light sources configured to direct light into the lens to be reflected from the plurality of reflective surfaces towards the eye.

5. The system of claim 1, further comprising a controller coupled to one or more light sources of the illumination source to modulate the brightness levels of the one or more light sources to provide desired brightness levels within a field-of-view of the eye-tracking camera.

6. The system of claim 5, wherein the controller is configured to illuminate a single light source to produce a single glint, and wherein the processor is configured for isolating the single glint in the gaze-tracking camera images.

7. The system of claim 1, wherein the eye-tracking cameras comprise one of a CCD and CMOS detector.

8. The system of claim 1, wherein the eye-tracking camera comprises an active area for generating eye-tracking camera images, and wherein the active area surface is curved.

9. The system of claim 1, further comprising a scene camera mounted on the device and positioned for viewing reference locations in the environment of the wearer, the processor coupled to the scene camera for acquiring scene images of the field of view and correlating the location of the features of the eye relative to the one or more glints to determine locations being viewed by the wearer within the scene images.

10. The system of claim 1, wherein the features of the eye comprise the eye's pupil.

11. A system for determining gaze-tracking locations, comprising:
a device configured to be worn on a wearer's head;
one or more illumination sources mounted on the device oriented to illuminate an eye of the wearer;
a plurality of eye-tracking cameras mounted on the device and positioned for viewing the eye; and
a processor coupled to the eye-tracking cameras for analyzing images of the eye acquired by the eye-tracking cameras to identify one or more glints reflected off the eye from the one or more illumination sources and identify the location of features of the eye relative to the one or more glints to determine locations being viewed by the wearer,
wherein the eye-tracking cameras are sufficiently spaced apart from one another such that the eye's pupil appears in eye-tracking camera images from at least one of the eye-tracking cameras when the eye moves through its complete normal range of motion.

12. The system of claim 11, further comprising a scene camera mounted on the device and positioned for viewing reference locations in the environment of the wearer, the processor coupled to the scene camera for acquiring scene images of the field of view and correlating the location of features of the eye relative to the one or more glints to determine locations being viewed by the wearer within the scene images.

13. A method for gaze tracking, comprising:
placing a device on a wearer's head, the device comprising one or more illumination sources and a plurality of eye-tracking cameras oriented towards an eye of the wearer, the eye-tracking cameras positioned at different locations on the device to provide overlapping fields-of-view of the eye; and
analyzing images of the eye acquired by the eye-tracking cameras to identify one or more glints reflected off the eye from the one or more illumination sources and identify the location of features of the eye relative to the one or more glints to determine locations being viewed by the wearer,
wherein the location of the features of the eye is monitored from the images of the eye-tracking cameras to identify an eye-tracking camera in which the features of the eye are closest to the center of the field-of-view relative to the other eye-tracking cameras, and wherein analyzing images of the eye comprises analyzing images from the identified eye-tracking camera to determine locations being viewed by the wearer.

14. The method of claim 13, further comprising periodically identifying an eye-tracking camera in which the features of the eye are closest to the center of the field-of-view relative to the other eye-tracking cameras, and comprises analyzing images from the identified eye-tracking camera to determine locations being viewed by the wearer.

15. The system of claim 13, wherein the features of the eye comprise the eye's pupil.

16. A method for gaze tracking, comprising:
placing a device on a wearer's head, the device comprising one or more illumination sources and a plurality of eye-tracking cameras oriented towards an eye of the wearer, the eye-tracking cameras positioned at different locations on the device to provide overlapping fields-of-view of the eye; and
analyzing images of the eye acquired by the eye-tracking cameras to identify one or more glints reflected off the eye from the one or more illumination sources and identify the location of features of the eye relative to the one or more glints to determine locations being viewed by the wearer,
wherein the location of the features of the eye is monitored from the images of the eye-tracking cameras, and wherein analyzing images of the eye comprises averaging the location of the features of the eye in the images to determine locations being viewed by the wearer.

17. The method of claim 16, further comprising applying corrective spatial mapping functions to the images to accommodate for at least one of spherical aberration and curvature of the eye.

18. The method of claim 16, wherein the location of the features of the eye from the images of the eye-tracking cameras is weighted prior to averaging to accommodate for at least one of spherical aberration and curvature of the eye.

* * * * *